(12) United States Patent
Amma et al.

(10) Patent No.: US 12,037,284 B2
(45) Date of Patent: Jul. 16, 2024

(54) OPTICAL GLASS, OPTICAL MEMBER, AND WEARABLE DEVICE

(71) Applicant: AGC INC., Tokyo (JP)

(72) Inventors: Shinichi Amma, Tokyo (JP); Tatsuo Nagashima, Tokyo (JP)

(73) Assignee: AGC INC., Tokyo (JP)

( * ) Notice: Subject to any disclaimer, the term of this patent is extended or adjusted under 35 U.S.C. 154(b) by 551 days.

(21) Appl. No.: 16/853,023

(22) Filed: Apr. 20, 2020

(65) Prior Publication Data

US 2020/0247712 A1 Aug. 6, 2020

Related U.S. Application Data

(63) Continuation of application No. PCT/JP2018/037092, filed on Oct. 3, 2018.

(30) Foreign Application Priority Data

Oct. 25, 2017 (JP) .................. 2017-206156

(51) Int. Cl.
*C03C 3/097* (2006.01)
*A61F 9/02* (2006.01)
*G02B 1/00* (2006.01)
*G02B 27/01* (2006.01)
(Continued)

(52) U.S. Cl.
CPC ................ *C03C 3/097* (2013.01); *A61F 9/02* (2013.01); *G02B 1/00* (2013.01); *G02B 27/0172* (2013.01); *G02C 7/02* (2013.01); *G02C 7/022* (2013.01); *C03C 4/00* (2013.01); *G02B 2027/0178* (2013.01)

(58) Field of Classification Search
CPC .. C03C 3/097; C03C 4/00; C03C 3/16; C03C 3/15; C03C 3/062; A61F 9/02; G02B 1/00; G02B 27/0172; G02B 2027/0178; G02B 1/14; G02C 7/02; G02C 7/022
See application file for complete search history.

(56) References Cited

U.S. PATENT DOCUMENTS

| | | | |
|---|---|---|---|
| 9,914,660 B2* | 3/2018 | Schreder | C03C 3/095 |
| 10,710,920 B2* | 7/2020 | Ellison | C03B 27/03 |
| 11,097,974 B2* | 8/2021 | Lezzi | C03B 29/16 |

(Continued)

FOREIGN PATENT DOCUMENTS

| | | |
|---|---|---|
| CN | 107108331 A | 8/2017 |
| JP | 2007-302550 A | 11/2007 |

(Continued)

OTHER PUBLICATIONS

European Extended Search Report, dated Jul. 16, 2021, issued in corresponding European Patent Application No. 18869938.3, (9 pages).

(Continued)

*Primary Examiner* — Balram T Parbadia
*Assistant Examiner* — Gabriel A Sanz
(74) *Attorney, Agent, or Firm* — Foley & Lardner LLP

(57) ABSTRACT

An optical glass has a refractive index ($n_d$) of 1.55 or more. A difference (Tf−Tg) between a fictive temperature (Tf) and a glass transition temperature (Tg) of the optical glass is 0° C. or more. The optical glass may have a crack initiation load L of 350 mN or more.

10 Claims, 1 Drawing Sheet

(51) Int. Cl.
*G02C 7/02* (2006.01)
*C03C 4/00* (2006.01)

(56) References Cited

U.S. PATENT DOCUMENTS

| | | | |
|---|---|---|---|
| 2005/0026768 A1 | 2/2005 | Shimizu et al. | |
| 2005/0028558 A1* | 2/2005 | Sato | C03C 17/22 65/32.1 |
| 2008/0300125 A1 | 12/2008 | Wolff et al. | |
| 2009/0082189 A1 | 3/2009 | Shimizu et al. | |
| 2011/0123833 A1 | 5/2011 | Endo et al. | |
| 2016/0251255 A1* | 9/2016 | Gross | C03C 21/002 428/332 |
| 2017/0183255 A1* | 6/2017 | Walther | C03C 3/091 |
| 2017/0305789 A1 | 10/2017 | Fujii et al. | |
| 2018/0244559 A1 | 8/2018 | Akiba et al. | |
| 2019/0055150 A1* | 2/2019 | Fabian | C03B 20/00 |
| 2019/0185365 A1* | 6/2019 | Kitamura | C03B 37/027 |

FOREIGN PATENT DOCUMENTS

| | | |
|---|---|---|
| JP | 2008-297198 A | 12/2008 |
| JP | 2010-265124 A | 11/2010 |
| JP | 2011-108344 A | 6/2011 |
| WO | WO-2004/110942 A1 | 12/2004 |
| WO | WO-2017/090645 A1 | 6/2017 |

OTHER PUBLICATIONS

Gross, et al., "Fictive temperature of $GeO_2$ glass: Its determination by IR method and its effects on density and refractive index", Journal of Non-Crystalline Solids 353(52-54): 4762-4766 (2007).

International Search Authority, "International Search Report," issued in connection with International Patent Application No. PCT/JP2018/037092, daed Jan. 8, 2019.

International Searching Authority, "Written Opinion," Issued in connection with International Patent Application No. PCT/JP2018/037092, dated Jan. 8, 2019.

Wang Yingjun, et al., "New Spectacle Glass Technology", New Materials Science and Technology Inorganic Materials, South China University of Technology Press, vol. 1, Oct. 2016, p. 345.

AGC, High refractive index & high transmittance glass substrates for "AR (Augmented reality) glasses and smart glasses," https://www.agc.com/en/products/electoric/detail/high-refractive-index.html (Accessed Aug. 9, 2022).

Blackman, A., "Glass lenses in modern dispensing," Dispensing Optics, Aug. 2013, https://www.abdo.org.uk/wp-content/uploads/2012/06/CET139.pdf.

Badrinarayanan et al., "The glass transition temperature versus the fictive temperature", ScienceDirect, Journal of Non-Crystalline Solids 353, Jun. 11, 2007, pp. 2603-2612.

Spinner et al., "Determination and Use of the Sag Point as a Reference Point in the Heating of Glasses", Journal of Research of the National Bureau of Standards, vol. 59, No. 3, Sep. 1957, pp. 227-231.

* cited by examiner

OPTICAL GLASS, OPTICAL MEMBER, AND WEARABLE DEVICE

CROSS-REFERENCE TO RELATED APPLICATIONS

This is a bypass continuation of PCT Application No. PCT/JP2018/037092, filed on Oct. 3, 2018, which claims priority to Japanese Application No. 2017-206156, filed on Oct. 25, 2017. The contents of these applications are hereby incorporated by reference in their entireties.

TECHNICAL FIELD

The present invention relates to an optical glass, an optical member, and a wearable device.

BACKGROUND ART

The glass used for wearable device such as glasses with projector, glasses-type or goggle-type display, virtual reality and augmented reality display device, and virtual image display device is required to have high refractive index from the viewpoint of, for example, realizing a wide angle and high luminance/high contrast of image, enhancing the light guide properties, and facilitating the processing of diffraction grating. Also a small-sized imaging glass lens with a wide imaging angle of view has been conventionally used in applications such as vehicle-mounted camera and robot's visual sensor, and a high refractive index is required of such an imaging glass lens so as to photograph a wider range with a smaller lens.

An in-vehicle camera or robot is expected to be used in a high-speed moving or harsh environment and therefore, an imaging glass lens mounted on an in-vehicle camera, etc. is required to have a significantly higher strength than that of an imaging lens of a general camera. For example, the in-vehicle camera is required to be free from an occurrence of damage, corrosion, etc. due to an impact or window pressure involved with car running or a dust splashed in the running.

The wearable device is also expected to encounter a scene in which, for example, the user accidentally drops the device or the dirt such as sebum or sandy dust is wiped off, and therefore, as with the lens for in-vehicle camera, a high-strength glass is required of the light guide plate, glass with diffraction grating or eyeglass lens to be mounted.

As such a high-refractive-index optical glass, an optical glass in which the crack initiation load (CIL) or fracture toughness is improved (see, for example, Patent Literature 1), etc. are known.

A glass substrate in which the strength is improved by raising the fictive temperature (see, for example, Patent Literatures 2 and 3) is known.

CITATION LIST

Patent Literature

Patent Literature 1: International Publication No. 2017/090645
Patent Literature 2: JP-A-2007-302550
Patent Literature 3: JP-A-2011-108344

SUMMARY OF INVENTION

Technical Problem

However, Patent Document 1 describes an optical glass in which the strength is improved by taking into account mainly the glass composition. Furthermore, the glass substrates of Patent Literatures 2 and 3 are used for an information recording medium and have a low refractive index but are not intended for optical glass applications.

In optical glass applications, the glass is generally produced through precise annealing so as to make a dense and distortion-free glass, because its properties are ensured, and the fictive temperature of the optical glass is lower than the glass transition temperature.

The present invention has been invented to solve the above-described problems, and an object thereof is to provide an optical glass having more enhanced strength than ever before and ensuring good product characteristics.

Solution to Problem

The optical glass of the present invention is an optical glass having a refractive index ($n_d$) of 1.55 or more and is characterized in that a difference (Tf–Tg) between a fictive temperature (Tf) and a glass transition temperature (Tg) of the optical glass is 0° C. or more.

The optical member and wearable device of the present invention are characterized by using the optical glass of the present invention.

Advantageous Effects of Invention

According to the optical glass of the present invention, an optical glass having a high refractive index and high strength can be provided. Therefore, by virtue of using the optical glass, the optical member and the wearable device can be a product protected from damage due to dropping, etc.

DESCRIPTION OF EMBODIMENTS

Figure 1:
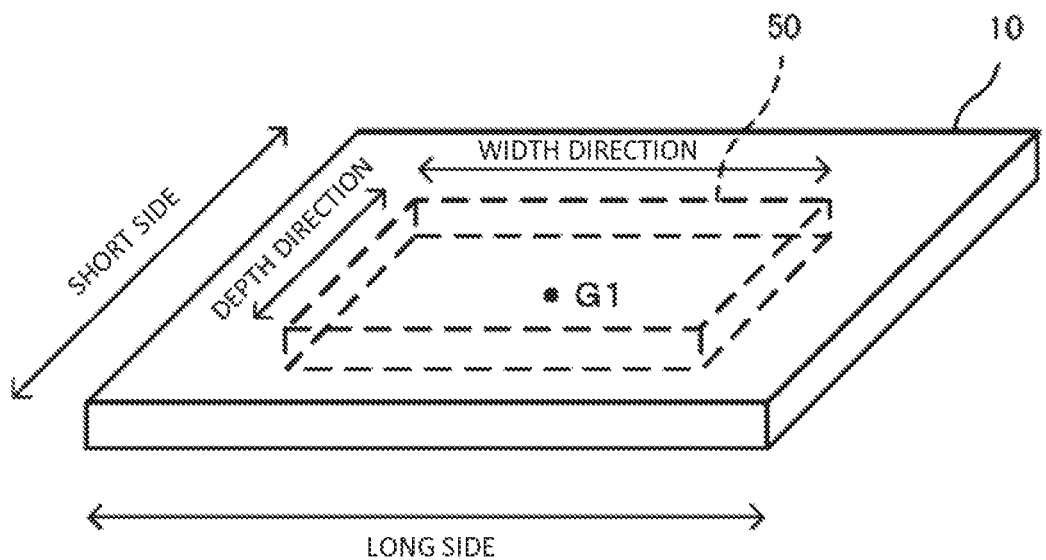
FIG. 1 is a diagram for explaining the measurement sample in measuring the optical glass properties.

Embodiments of the optical glass, optical member and wearable device of the present invention are described below.

An optical glass of this embodiment has, as described above, a predetermined refractive index ($n_d$), and a fictive temperature (Tf) and a glass transition temperature (Tg) of the optical glass satisfy a predetermined relationship. These properties are described in sequence.

The optical glass of this embodiment has a high refractive index ($n_d$) of 1.55 or more. Since the refractive index ($n_d$) is 1.55 or more, the optical glass of this embodiment is suitable as an optical glass used in a wearable device in terms of, for example, achieving a wide angle and high luminance/high contrast of an image, enhancing the light guide properties, and facilitating the processing of diffraction grating. In addition, the optical glass is suitable as a small imaging glass lens having a wide imaging angle of view used for applications such as in-vehicle camera and robotic vision sensor, because a wide range is photographed by a smaller lens. The refractive index ($n_d$) is preferably 1.60 or more, more preferably 1.65 or more, still more preferably 1.68 or more, yet still more preferably 1.72 or more, even yet still more preferably 1.74 or more, more preferably 1.76 or more, still more preferably 1.78 or more, especially preferably 1.80 or more.

On the other hand, the glass having a too large refractive index ($n_d$) tends to allow an easy increase in the density and also an easy increase in the devitrification temperature. Therefore, the refractive index ($n_d$) is preferably 2.20 or less, more preferably 2.00 or less, still more preferably 1.90 or less, yet still more preferably 1.86 or less, even yet still more preferably 1.84 or less, more preferably 1.82 or less, still more preferably 1.81 or less, especially preferably 1.80 or less.

In the optical glass of this embodiment, the difference (Tf−Tg) between the fictive temperature (Tf) and the glass transition temperature (Tg) is 0° C. or more. By satisfying such a relationship, the glass structure is made sparser and even when some impact is applied to the optical glass, the glass structure is densified to facilitate the absorption of the impact. As a result, when formed into a product, an optical glass capable of suppressing damage due to dropping, etc. (the strength is enhanced) is obtained.

As for the optical glass of Tf−Tg≥0, the cooling rate in the temperature region from (Tg+100° C.) to around (Tg−150° C.) relating to the fictive temperature is set to be 2° C./min or more. The cooling rate is preferably 5° C./min or more, more preferably 10° C./min or more, still more preferably 20° C./min or more, still more preferably 50° C./min or more, still more preferably 75° C./min or more, especially preferably 100° C./min or more. The upper limit need not be particularly limited but is, for example, 500° C./min or less. By adjusting the cooling rate above, the fictive temperature of the optical glass can be adjusted.

As for the conventional optical glass, in the production process thereof, the glass is annealed by precise annealing and solidified to make a product and therefore, its Tf is generally lowered and is lower than Tg. In this embodiment, the Tf was studied, as a result, it has been found that when the fictive temperature is made equal to or higher than Tg, that is, when the difference (Tf−Tg) between Tf and Tg of the optical glass is set to be 0° C. or more, the strength of the optical glass itself can be enhanced and damage due to dropping, etc. can be suppressed. The difference (Tf−Tg) is preferably 5° C. or more, more preferably 10° C. or more, still more preferably 15° C. or more, yet still more preferably 20° C. or more, even yet still more preferably 25° C. or more, more preferably 30° C. or more, still more preferably 40° C. or more, yet still more preferably 50° C. or more. In order to obtain the effect of strength enhancement, it is not necessary to dare to set the upper limit of the difference (Tf−Tg), but when the difference (Tf−Tg) is 100° C. or less, the cooling rate of the glass can be kept low, and the warpage or plate thickness deviation of the glass is improved. In the case where improvement of the warpage or plate thickness deviation of the glass is also required, the difference (Tf−Tg) is preferably 70° C. or less, more preferably 50° C. or less, still more preferably 40° C. or less, yet still more preferably 30° C. or less.

The glass at a high temperature has a low viscosity and is in a liquid state. The glass structure here is in a sparse state. As the glass is cooled, the glass structure is solidified while becoming dense. This structural change in the glass is caused in the process of the glass undergoing transition to a most stable state at that temperature. However, when the cooling rate of the glass is large, the glass structure is frozen before becoming a dense structure corresponding to the temperature, and the structure of the glass is fixed in the state of the high temperature side. The temperature corresponding to the solidified glass structure is referred to as the fictive temperature. More specifically, even if the glass has exactly the same composition, Tf differs depending on the heat treatment in the production process. In this way, the glass structure varies according to the heat temperature, and the physical properties of the glass also differ.

The Tf can be determined by a known measurement method such as calorimetric method or heat shrinkage measurement. In this description, the Tf measurement method conducted in practice is described in detail in Examples.

In addition, Tg of the optical glass can be determined, for example, by a known method such as thermal expansion method.

The Tg of the optical glass of this embodiment is preferably 800° C. or less. When the optical glass of this embodiment has Tg in the range above, the moldability in press molding and redraw forming is good. The Tg is more preferably 760° C. or less, still more preferably 720° C. or less, yet still more preferably 680° C. or less, especially preferably 640° C. or less.

Tg of the optical glass of this embodiment is preferably 500° C. or more. When the optical glass of this embodiment has Tg in the range above, it becomes easy to increase the cooling rate near Tg and raise the fictive temperature. The Tg is more preferably 520° C. or more, still more preferably 540° C. or more, yet still more preferably 560° C. or more, especially preferably 580° C. or more.

Furthermore, from the viewpoint of enhancing the strength by satisfying the above-described properties, the optical glass of this embodiment preferably has the following properties.

The Young's modulus (E) of the optical glass of this embodiment is preferably 60 GPa or more. Having such a property is advantageous in that when the optical glass is used as a thin glass plate for a wearable device or used as a lens for an in-vehicle camera, robotic vision sensor, etc., deflection is less likely to occur.

From the viewpoint of reducing the deflection amount of the glass, the E is more preferably 70 GPa or more, still more preferably 80 GPa or more, yet still more preferably 85 GPa or more, especially preferably 90 GPa or more. When the Young's modulus (E) of the optical glass of this embodiment is 140 GPa or less, breakage is less likely to occur in the case where the cooling is performed at a high cooling rate so as to obtain a high fictive temperature. From the viewpoint of making the glass resistant to breakage, the E is more preferably 120 GPa or less, still more preferably 100 GPa or less, yet still more preferably 95 GPa or less, especially preferably 90 GPa or less.

The coefficient of thermal expansion (α) at 50 to 350° C. of the optical glass of this embodiment is preferably 50 ($\times 10^{-7}$/K) or more. When the optical glass of this embodiment has α in the range above, the expansion matching to peripheral members is good. The α is more preferably 60 ($\times 10^{-7}$/K) or more, still more preferably 70 ($\times 10^{-7}$/K) or more, yet still more preferably 80 ($\times 10^{-7}$/K) or more, especially preferably 90 ($\times 10^{-7}$/K) or more.

The α of the optical glass of this embodiment is preferably 150 ($\times 10^{-7}$/K) or less. When the optical glass of this embodiment has α in the range above, breakage during cooling is less likely to occur and therefore, the cooling rate can be increased, making it possible to adjust the difference (Tf−Tg) between Tf and Tg of the optical glass to be 0° C. or more, namely, raise Tf of the glass compared with Tg. Consequently, the glass structure is made sparser and even when some impact is applied to the optical glass, the glass structure is densified to facilitate the absorption of the impact. As a result, the strength of the optical glass itself can be enhanced, and damage due to dropping, etc. can be suppressed. The α is more preferably 120 (×10$^{-7}$/K) or more, still more preferably 110 (×10$^{-7}$/K) or less, yet still more preferably 100 (×10$^{-7}$/K) or less, especially preferably 95 (×10$^{-7}$/K) or less.

In the optical glass of this embodiment, when the maximum thickness is 2.0 mm or less, it becomes easy to increase the cooling rate and raise the fictive temperature. The thickness is more preferably 1.5 mm or less, still more preferably 1.0 mm or less, yet still more preferably 0.8 mm or less, especially preferably 0.6 mm or less. In order to increase the cooling rate and raise the fictive temperature, it is not necessary to dare to set the lower limit of the thickness, but when the maximum thickness is 0.01 mm or more, deflection due to own weight of the optical glass can be reduced. The thickness is more preferably 0.1 mm or more, still more preferably 0.3 mm or more, yet still more preferably 0.5 mm or more, especially preferably 0.7 mm or more.

The optical glass of this embodiment is preferably in a glass plate shape. In the case of a glass plate, the area of one main surface thereof is preferably 8 cm$^2$ or more. When the area is 8 cm$^2$ or more, a large number of optical elements can be disposed, and the productivity is enhanced. The area is more preferably 30 cm$^2$ or more, still more preferably 170 cm$^2$ or more, yet still more preferably 300 cm$^2$ or more, especially preferably 1,000 cm$^2$ or more. On the other hand, when the area is 6,500 cm$^2$ or less, handling of the glass plate is facilitated, and the breakage during handling or processing of the glass plate can be suppressed. The area is more preferably 4,500 cm$^2$ or less, still more preferably 4,000 cm$^2$ or less, yet still more preferably 3,000 cm$^2$ or less, especially preferably 2,000 cm$^2$ or less.

The surface roughness Ra of one main surface of the optical glass of this embodiment is preferably 2 nm or less. When Ra is in this range, a nanostructure having the desired shape can be formed on one main surface by using imprint technology, etc., and desired light guide properties are also obtained. Ra is more preferably 1.7 nm or less, still more preferably 1.4 nm or less, yet still more preferably 1.2 nm or less, especially preferably 1.0 nm or less. Here, the surface roughness Ra is an arithmetic mean roughness defined in JIS B0601 (2001). In this description, the surface area is a value obtained by measuring three different areas of 10 μm×10 μm by means of an atomic force microscope (AFM) and averaging the results.

In the optical glass of this embodiment, the difference (Δn) between the maximum value and the minimum value of the refractive index in a cross-section of the glass plate is preferably 5.0×10$^{-5}$ or less.

In this description, the cross-section of the glass plate indicates a cross-section exposed by cutting the glass plate from one main surface to another main surface in the plate thickness direction and indicates, in the below-described measurement of Δn, a polished side surface of a measurement sample obtained by further polishing a sample cut out in a predetermined size from a molded body.

The measurement of Δn can be performed by a known method, for example, by the following procedure using a transmission-type two-beam interference microscope.

[Measurement Method of Δn]

<Preparation of Measurement Sample>

Figure 2:
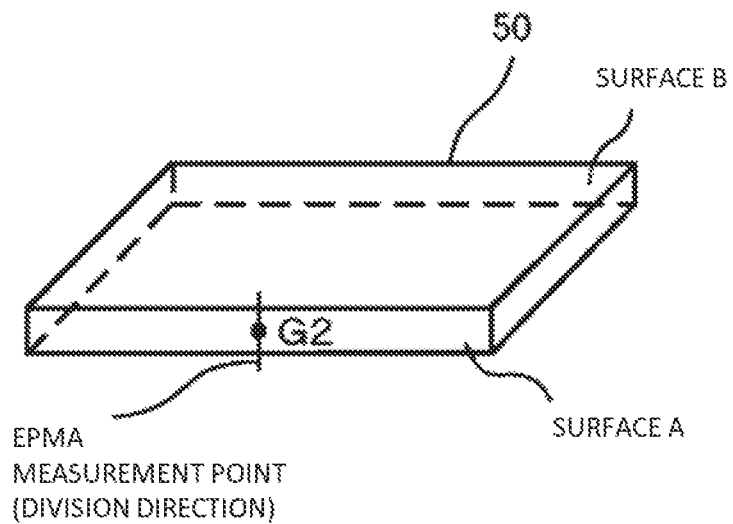
FIG. 2 is a diagram for explaining the measurement sample in measuring the optical glass properties.

An optical glass is obtained as a plate-like molded body, and a sample having a width of 30 mm and a depth of 10 mm (the plate thickness is unchanged) is cut out from the molded body such that the center-of-gravity (G1) positions of the molded body and the sample coincide and the long-side direction of the molded body becomes parallel to the width direction of the sample (see FIG. 1). FIG. 2 illustrates the cut-out sample, and two side surfaces extending in the width direction are designated as surface A and surface B, respectively.

Next, surface A and surface B of the sample are ground using a diamond wheel as a grinding stone. The grinding is performed, as shown in Table 1, in four stages in sequence from first stage to fourth stage while changing the grinding amounts of surface A and surface B and the mesh size of the diamond wheel.

Subsequently, surfaces A and B of the sample after grinding is mirror-polished using a diamond slurry to obtain a measurement sample. The polishing amount here is 10 μm or more, and as the diamond slurry, for example, a slurry containing 0.1 mass % of single crystal diamond of mesh size #14000 is used.

The cross-section of the glass plate in one embodiment of the present invention corresponds to surface A or B of the measurement sample obtained according to the above-described procedure.

TABLE 1

| | Grinding Amount of each of Surface A and Surface B | Mesh Size of Diamond Wheel |
|---|---|---|
| First stage | 2,000 μm or more | #100 |
| Second stage | 200 μm or more | #400 |
| Third stage | 100 μm or more | #1000 |
| Fourth stage | 50 μm or more | #2000 |

<Measurement of Δn>

In the measurement of Δn, a transmission-type two-beam interference microscope is used. In the later-described Examples, Δn in the plate thickness direction of the measurement sample was measured at a space resolution of 9.1 μm×9.1 μm (corresponding to CCD camera four pixels) by using a transmission-type two-beam interference microscope (TD series) manufactured by Mizojiri Kogaku Kogyosho K.K. and using 546 nm (light source: xenon lamp, monochromatic filter: 546 nm) as a measurement wavelength.

At the time of measuring a minute refractive index difference, factors possibly adversely affecting the measurement accuracy need to be eliminated. For example, it is necessary to suppress the temperature variation around the apparatus, prevent the vibration, and shield the external light (e.g., illumination).

Furthermore, depending on the objective lens used, the measurement accuracy may differ or an accuracy distribution may be produced within the measurement plane. Therefore, the phase difference distribution (plane tilt correction) is measured in the state of none being present on the light path, and the plane tilt correction is performed such that the difference between the maximum value and the minimum value within the measurement plane becomes 1/100λ or less (5 nm or less).

The measurement sample is then placed by arranging the depth direction to become a light path, and the phase difference distribution is measured under the above-described conditions (plane tilt correction). The depth of the measurement sample (the length from surface A to surface B) is measured by a micrometer, and the refractive index distribution (=phase difference distribution/depth) is calculated from the phase difference distribution. The depth is the length at the center of gravity (G2) of surface A.

On the mirror-polished surface A, the refractive index distribution is calculated along a line (plate thickness direction) passing the center of gravity (G2) of surface A and being perpendicular to the main surface, and the difference between the maximum value and the minimum value thereof is defined as Δn.

When Δn is $5.0 \times 10^{-5}$ or less, the optical glass of this embodiment is suitable for use as a light guide plate employed in a wearable device in terms of achieving sharpness and high luminance/high contrast of an image, enhancing the light guide properties, and facilitating the processing of diffraction grating. The difference between the maximum value and the minimum value of the refractive index is more preferably $3.0 \times 10^{-5}$ or less, still more preferably $2.0 \times 10^{-5}$ or less, yet still more preferably $1.0 \times 10^{-5}$ or less, especially preferably $0.5 \times 10^{-5}$ or less.

In the cross-section of the measurement sample obtained as above, the refractive index indicator value N can also be calculated as follows. More specifically, in the cross-section of the measurement sample, the refractive index indicator value N can be calculated using the following formula (1), and the difference between the maximum value ($N_{max}$) and the minimum value ($N_{min}$) of the calculated refractive index indicator value N is preferably $5.0 \times 10^{-3}$ or less. As seen from formula (1), the refractive index indicator value N depends on the composition (the concentration of the oxide contained).

$$N = A_{Si} \times C_{Si} + A_{Al} \times C_{Al} + A_{Pt} \times C_{Pt} + A_{Zr} \times C_{Zr} \quad (1)$$

(in the formula, $C_{Si}$: concentration (mol %) of $SiO_2$, $C_{Al}$: concentration (mol %) of $Al_2O_3$, $C_{Pt}$: concentration (mol %) of $PtO_2$, $C_{Zr}$: concentration (mol %) of $ZrO_2$, $A_{Si}=1.4$, $A_{Al}=1.4$, $A_{Pt}=5.0$, and $A_{Zr}=2.0$).

The refractive index indicator value N is a value obtained by irradiating surface A of the measurement sample prepared for the measurement of Δn with light in the same direction as the light path of the phase difference distribution, along a line passing the center of gravity (G2) of surface A and being perpendicular to the main surface (thickness direction), for each of sections equally divided in the plate thickness direction, and measuring the numerical value (see FIG. 2). The number of sections is 20 at the minimum and can be arbitrarily increased so as to raise the resolution. Furthermore, $C_{Si}$, $C_{Al}$, $C_{Pt}$ and $C_{Zr}$ are numerical values obtained by converting the values measured for each element by an electron probe micro analyzer (EPMA) to each oxide concentration in mol %. $A_{Si}$, $A_{Al}$, $A_{Pt}$ and $A_{Zr}$ are correction values for calculating the refractive index indicator values N of respective oxides.

When the difference between the maximum value and the minimum value of N is $5.0 \times 10^{-3}$ or less, the optical glass of this embodiment is suitable for use as a light guide plate employed in a wearable device in terms of achieving sharpness and high luminance/high contrast of an image, enhancing the light guide properties, and facilitating the processing of diffraction grating. The difference between the maximum value and the minimum value of the refractive index is more preferably $3.0 \times 10^{-3}$ or less, still more preferably $2.0 \times 10^{-3}$ or less, yet still more preferably $1.0 \times 10^{-3}$ or less, especially preferably $5.0 \times 10^{-4}$ or less.

The optical glass of this embodiment preferably has a crack initiation load L of 350 mN or more. Here, the crack initiation load in this embodiment can be obtained by the following method.

In a constant temperature and humidity bath kept at a humidity of 30% and a temperature of 25° C., a Vickers indenter set at a load of 10, 25, 50, 100 and 200 g is pressed against the glass surface (optical polished surface) for 15 seconds, and after 15 seconds, the number of cracks generated from four corners of the indentation is counted (4 cracks at the maximum per one indentation). The pressing is repeated 20 times (that is, the indenter is pressed 20 times) at each load, and after counting the total number of cracks, the crack initiation rate is determined by total number of crack initiations/80. The obtained crack initiation rate is potted vs. load, and the load at which the crack initiation rate becomes 50% when fitting a sigmoid function by means of the least squares method is defined as the crack initiation load L.

In the optical glass of this embodiment, the difference (L−L0) between its crack initiation load L and the crack initiation load L0 of a glass having the same composition as the optical glass above and being obtained through precise annealing after melting is preferably 98 mN or more, more preferably 150 mN or more, still more preferably 200 mN or more, yet still more preferably 250 mN or more, even yet still more preferably 300 mN or more.

Here, the crack initiation load L0 is a value obtained by performing the same test as the calculation of the crack initiation load L on a glass having the same composition as the optical glass above and being obtained through precise annealing after melting.

The precise annealing as used herein is an operation in which the optical glass is put in a box-type electric furnace, heated up to Tg+30° C. (a temperature 30° C. higher than the glass transition temperature), kept for 1 hour, cooled to Tg−150° C. (a temperature 150° C. lower than the glass transition temperature) at a cooling rate of 0.1° C./min under program control, and allowed to naturally cool.

[Glass Components]

One embodiment of the composition range of each component that can be contained in the optical glass of this embodiment is described in detail below. In this description, unless otherwise indicated, the content of each component is represented by mass % relative to the total mass of the glass matrix composition based on oxides. Here, the glass matrix composition are components excluding $Sb_2O_3$ and $SnO_2$.

The matrix composition satisfying the properties of high refractive index, good light transmittance and high meltability in the optical glass of this embodiment includes, for example, a composition containing, in mass % based on oxides, as the glass forming component, from 5 to 80 mass % of at least one selected from the group consisting of $SiO_2$, $B_2O_3$ and $P_2O_5$, as the modifier oxide, 5 to 70 mass % in a total amount of at least one oxide selected from the group consisting of MgO, CaO, SrO, BaO, ZnO, $Li_2O$, $Na_2O$, $K_2O$, $Cs_2O$ and $Ln_2O_3$ (Ln is at least one selected from the group consisting of Y, La, Gd, Yb and Lu), and as the intermediate oxide, 0 to 50 mass % in a total amount of at least one oxide selected from the group consisting of $Al_2O_3$, $TiO_2$, $ZrO_2$, $WO_3$, $Bi_2O_3$, $TeO_2$, $Ta_2O_5$ and $Nb_2O_5$.

Examples of the optical glass having such a composition include, specifically, (1) an La—B-based optical glass, (2) an $SiO_2$-based optical glass, and (3) a $P_2O_5$-based optical glass. In the description of contents in the glass composition, simple expressions "%" and "ppm" mean "mass %" and "ppm by mass" unless specifically stated.

Examples of (1) the La—B-based optical glass include a glass containing from 5 to 70% of $La_2O_3$ and from 5 to 70% of $B_2O_3$ assuming the total of the matrix composition is 100%.

By containing 5% or more of $La_2O_3$ component, a desired high refractive index can be achieved, and the dispersion can be reduced (the Abbe number can be increased). Accordingly, the lower limit of the content of $La_2O_3$ component is preferably 10%, more preferably 15%, still more preferably 20%, yet still more preferably 30%.

On the other hand, when the content of $La_2O_3$ component is 70% or less, reduction in the meltability of the glass is prevented, and the devitrification resistance of the glass is enhanced. Accordingly, the upper limit of the content of $La_2O_3$ component is preferably 60%, more preferably 50%, still more preferably 40%, yet still more preferably 30%.

$B_2O_3$ is a glass forming component, and the $B_2O_3$ content is preferably from 5 to 70% assuming the total of the matrix composition is 100%.

By containing 5% or more of $B_2O_3$ component, the devitrification resistance of the glass is enhanced, and the dispersion of the glass can be reduced. Accordingly, the lower limit of the content of $B_2O_3$ component is preferably 10%, more preferably 20%, still more preferably 35%.

On the other hand, when the content of $B_2O_3$ component is 70% or less, a larger refractive index can be readily obtained, and deterioration of the chemical durability can be prevented. Accordingly, the upper limit of the content of $B_2O_3$ component is preferably 60%, more preferably 50%, still more preferably 40%, yet still more preferably 30%.

MgO is an optional component. The MgO content is preferably from 0 to 20% assuming the total of the matrix composition is 100%. By containing the MgO component, the mechanical strength of the glass can be enhanced. The MgO content is more preferably 1% or more, still more preferably 3% or more, yet still more preferably 5% or more, especially preferably 8% or more. When the MgO content is 20% or less, the devitrification temperature is lowered, and preferable production characteristics are obtained. The MgO content is more preferably 15% or less, still more preferably 10% or less, yet still more preferably 5% or less, especially preferably 3% or less.

CaO is an optional component. The CaO content is preferably from 0 to 30% assuming the total of the matrix composition is 100%. By containing the CaO component, the chemical durability of the glass can be enhanced. The CaO content is more preferably 1% or more, still more preferably 3% or more, yet still more preferably 5% or more, especially preferably 10% or more. When the CaO content is 30% or less, the devitrification temperature is lowered, and preferable production characteristics are obtained. The CaO content is more preferably 20% or less, still more preferably 15% or less, yet still more preferably 10% or less, especially preferably 5% or less.

SrO is an optional component. The SrO content is preferably from 0 to 30% assuming the total of the matrix composition is 100%. By containing the SrO component, the refractive index of the glass can be increased. The SrO content is more preferably 1% or more, still more preferably 3% or more, yet still more preferably 5% or more, especially preferably 10% or more. When the SrO content is 30% or less, the devitrification temperature is lowered, and preferable production characteristics are obtained. The SrO content is more preferably 20% or less, still more preferably 15% or less, yet still more preferably 10% or less, especially preferably 5% or less.

BaO is an optional component. The BaO content is preferably from 0 to 40% assuming the total of the matrix composition is 100%. By containing the BaO component, the refractive index of the glass can be increased. The BaO content is more preferably 1% or more, still more preferably 3% or more, yet still more preferably 5% or more, especially preferably 10% or more. When the BaO content is 40% or less, the devitrification temperature is lowered, and preferable production characteristics are obtained. The BaO content is more preferably 30% or less, still more preferably 20% or less, yet still more preferably 15% or less, especially preferably 10% or less.

ZnO is an optional component. The ZnO content is preferably from 0 to 30% assuming the total of the matrix composition is 100%. By containing the ZnO component, the refractive index of the glass can be increased. The ZnO content is more preferably 1% or more, still more preferably 3% or more, yet still more preferably 5% or more, especially preferably 10% or more. When the ZnO content is 30% or less, the devitrification temperature is lowered, and preferable production characteristics are obtained. The ZnO content is more preferably 20% or less, still more preferably 15% or less, yet still more preferably 10% or less, especially preferably 5% or less.

$Li_2O$ is an optional component. The $Li_2O$ content is preferably from 0 to 15% assuming the total of the matrix composition is 100%. When $Li_2O$ is contained, the strength (Kc) and crack resistance (CIL) can be enhanced. The $Li_2O$ content is more preferably 0.5% or more, still more preferably 1% or more, yet still more preferably 3% or more, especially preferably 5% or more. On the other hand, when the $Li_2O$ content is 15% or less, the devitrification temperature is lowered, and preferable production characteristics are obtained. The $Li_2O$ content is preferably 10% or less, more preferably 7% or less, still more preferably 5% or less, especially preferably 4% or less.

$Na_2O$ is an optional component. The $Na_2O$ content is from 0 to 20% assuming the total of the matrix composition is 100%. When the $Na_2O$ content is 20% or less, good crack resistance is obtained. The $Na_2O$ content is preferably 15% or less, more preferably 10% or less, still more preferably 7% or less, especially preferably 5% or less. In the case where the optical glass of this embodiment contains $Na_2O$, the devitrification temperature is lowered, and preferable production characteristics are obtained. The content thereof is preferably 0.5% or more, more preferably 1% or more, still more preferably 2% or more, especially preferably 3% or more.

$K_2O$ is an optional component. The $K_2O$ content is from 0 to 20% assuming the total of the matrix composition is 100%. When the $K_2O$ content is 20% or less, good crack resistance is obtained. The $K_2O$ content is preferably 15% or less, more preferably 10% or less, still more preferably 7% or less. In the case where the optical glass of this embodiment contains $K_2O$, the devitrification temperature is lowered, and preferable production characteristics are obtained. The content thereof is preferably 0.5% or more, more preferably 1% or more, still more preferably 2% or more, especially preferably 3% or more.

The optical glass of this embodiment can contain, as an optional component, alkali metal components ($Li_2O+Na_2O+K_2O$). The content of $Li_2O+Na_2O+K_2O$ is from 0 to 20% assuming the total of the matrix composition is 100%. When $Li_2O+Na_2O+K_2O$ is 2% or more, $T_2$ at which the viscosity of the glass is log $\eta=2$ is readily lowered, the melting temperature is low, and coloration is controlled. The content of $Li_2O+Na_2O+K_2O$ is preferably 4% or more, more preferably 6% or more, still more preferably 8% or more, especially preferably 10% or more. When the content of $Li_2O+Na_2O+K_2O$ is 20% or less, the devitrification temperature is lowered, and preferable production characteristics are obtained. The content of $Li_2O+Na_2O+K_2O$ is preferably 15% or less, more preferably 10% or less, still more preferably 8% or less, especially preferably 6% or less.

In the optical glass of this embodiment, among alkali metal components ($Li_2O$, $Na_2O$, $K_2O$), $Li_2O$ is a component capable of enhancing the strength of the glass, but if its amount is too large, $T_2$ is readily lowered, and devitrification is likely to occur. Accordingly, in the optical glass of this embodiment, the value of the ratio $Li_2O/(Li_2O+Na_2O+K_2O)$ is preferably 0.45 or less in mass % based on oxides. When $Li_2O/(Li_2O+Na_2O+K_2O)$ is 0.45 or less, $T_2$ is likely to be high, devitrification is less likely to occur, and ease of formability of the glass is enhanced. $Li_2O/(Li_2O+Na_2O+K_2O)$ is more preferably 0.4 or less, still more preferably 0.35 or less, especially preferably 0.3 or less.

$Cs_2O$ is an optional component. The $Cs_2O$ content is preferably from 0 to 20% assuming the total of the matrix composition is 100%. When the $Cs_2O$ content is more than 0%, the devitrification temperature is lowered, and preferable production characteristics are obtained. In the case where the optical glass of this invention contains $Cs_2O$, its content is preferably 0.5% or more, more preferably 1% or more, still more preferably 2% or more, especially preferably 3% or more. On the other hand, when the $Cs_2O$ content is 20% or less, good crack resistance is obtained. The $Cs_2O$ content is preferably 15% or less, more preferably 10% or less, still more preferably 7% or less.

$Ln_2O_3$ (Ln is at least one selected from the group consisting of Y, La, Gd, Yb and Lu) is an optional component. The content in terms of the total amount of $Ln_2O_3$ is from 0 to 55% assuming the total of the matrix composition is 100%. When $Ln_2O_3$ is contained, the refractive index of the glass can be increased. The content in terms of the total amount of $Ln_2O_3$ is preferably 1% or more, more preferably 5% or more, still more preferably 10% or more, especially preferably 15% or more.

When the $Ln_2O_3$ content is 55% or less, the devitrification temperature can be lowered, and the raw material cost can be reduced. Accordingly, the content in terms of the total amount is preferably 55% or less, more preferably 25% or less, still more preferably 15% or less, especially preferably 10% or less.

$Al_2O_3$ is an optional component. The $Al_2O_3$ content is from 0 to 55% assuming the total of the matrix composition is 100%. When $Al_2O_3$ is contained, the strength of the glass can be increased, and the stability of the glass can be enhanced. The $Al_2O_3$ content is preferably 1% or more, more preferably 3% or more, still more preferably 5% or more, especially preferably 8% or more.

When the $Al_2O_3$ content is 55% or less, the devitrification temperature is lowered, and preferable production characteristics are obtained. The $Al_2O_3$ content is preferably 15% or less, and it is preferred to have an $Al_2O_3$ content of 10% or less, furthermore, an $Al_2O_3$ content of 8% or less, particularly, an $Al_2O_3$ content of 5% or less.

$TiO_2$ is an optional component. The $TiO_2$ content is from 0 to 55% assuming the total of the matrix composition is 100%. When $TiO_2$ is contained, the refractive index of the glass can be increased, and the stability of the glass can be enhanced. The $TiO_2$ content is preferably 1% or more, more preferably 5% or more, still more preferably 10% or more, especially preferably 15% or more.

When the $TiO_2$ content is 55% or less, the devitrification temperature is lowered, and coloration of the glass is controlled. The $TiO_2$ content is preferably 35% or less, more preferably 25% or less, still more preferably 15% or less, especially preferably 10% or less.

$ZrO_2$ is an optional component. The $ZrO_2$ content is from 0 to 55% assuming the total of the matrix composition is 100%. When $ZrO_2$ is contained, the refractive index of the glass can be increased, and the chemical durability can be enhanced. The $ZrO_2$ content is preferably 1% or more, more preferably 5% or more, still more preferably 10% or more, especially preferably 15% or more.

When the $ZrO_2$ content is 55% or less, the devitrification temperature is lowered, and preferable production characteristics are obtained. The $ZrO_2$ content is preferably 30% or less, more preferably 20% or less, still more preferably 15% or less, especially preferably 10% or less.

$WO_3$ is an optional component. The $WO_3$ content is from 0 to 55% assuming the total of the matrix composition is 100%. When $WO_3$ is contained, the refractive index of the glass can be increased. The $WO_3$ content is preferably 1% or more, more preferably 3% or more, still more preferably 5% or more, especially preferably 10% or more.

When the $WO_3$ content is 55% or less, the devitrification temperature is lowered, and coloration of the glass is controlled. The $WO_3$ content is preferably 30% or less, more preferably 20% or less, still more preferably 15% or less, especially preferably 10% or less.

$Bi_2O_3$ is an optional component. The $Bi_2O_3$ content is from 0 to 55% assuming the total of the matrix composition is 100%. When $Bi_2O_3$ is contained, the refractive index of the glass can be increased. The $Bi_2O_3$ content is preferably 1% or more, more preferably 5% or more, especially preferably 10% or more.

When the $Bi_2O_3$ content is 55% or less, the devitrification temperature is lowered, and coloration of the glass can is controlled. The $Bi_2O_3$ content is preferably 35% or less, more preferably 25% or less, still more preferably 15% or less, especially preferably 10% or less.

$TeO_2$ is an optional component. The $TeO_2$ content is from 0 to 30% assuming the total of the matrix composition is 100%. When $TeO_2$ is contained, the refractive index of the glass can be increased. The $TeO_2$ content is preferably 1% or more, more preferably 5% or more, still more preferably 10% or more, especially preferably 15% or more.

When the $TeO_2$ content is 55% or less, the devitrification temperature can be lowered and moreover, the material cost can be reduced. The $TeO_2$ content is preferably 30% or less, more preferably 20% or less, still more preferably 15% or less, especially preferably 10% or less.

$Ta_2O_5$ is an optional component. The $Ta_2O_5$ content is from 0 to 30% assuming the total of the matrix composition is 100%. When $Ta_2O_5$ is contained, the refractive index of the glass can be increased. The $Ta_2O_5$ content is preferably 1% or more, more preferably 5% or more, still more preferably 10% or more, especially preferably 15% or more.

When the $Ta_2O_5$ content is 30% or less, the devitrification temperature can be lowered and moreover, the material cost can be reduced. The $Ta_2O_5$ content is preferably 25% or less, more preferably 20% or less, still more preferably 15% or less, especially preferably 10% or less.

$Nb_2O_5$ is an optional component. The $Nb_2O_5$ content is from 0 to 55% assuming the total of the matrix composition is 100%. When $Nb_2O_5$ is contained, the refractive index of the glass can be increased. The $Nb_2O_5$ content is preferably 5% or more, more preferably 10% or more, still more preferably 15% or more, especially preferably 30% or more.

When the $Nb_2O_5$ content is 55% or less, the devitrification temperature can be lowered and moreover, the material cost can be reduced. The $Nb_2O_5$ content is preferably 35% or less, more preferably 25% or less, still more preferably 15% or less, especially preferably 10% or less.

Examples of (2) the $SiO_2$-based optical glass include a glass containing from 10 to 70% of $SiO_2$ and containing, as the high refractive index component, 1% or more of at least one selected from the group consisting of $Nb_2O_5$, $Ta_2O_5$, $Li_2O$, SrO, BaO, $TiO_2$, $ZrO_2$, $WO_3$, $Bi_2O_3$, $TeO_2$ and $Ln_2O_3$ (Ln is at least one selected from the group consisting of Y, La, Gd, Yb and Lu).

$SiO_2$ is a glass forming component. The $SiO_2$ content is from 10 to 70% assuming the total of the matrix composition is 100%. When the $SiO_2$ content is 10% or more, the viscosity of the glass can let the temperature $T_2$ at which log η=2 be in the preferred range, high strength and crack resistance are imparted to the glass, and the stability and chemical durability of the glass can be enhanced. The $SiO_2$ content is preferably 15% or more, more preferably 20% or more, still more preferably 25% or more. On the other hand, when the $SiO_2$ content is 70% or less, a component for obtaining a high refractive index can be contained. The $SiO_2$ content is preferably 60% or less, more preferably 50% or less, still more preferably 40% or less.

$Nb_2O_5$ is an optional component. When the $Nb_2O_5$ content is 5% or more assuming the total of the matrix composition is 100%, the refractive index of the glass can be increased and the Abbe number ($v_d$) can be reduced. The $Nb_2O_5$ content is more preferably 15% or more, still more preferably 25% or more, especially preferably 30% or more.

When the $Nb_2O_5$ content is 70% or less, the devitrification temperature can be lowered and moreover, the raw material cost can be reduced. The $Nb_2O_5$ content is preferably 60% or less, more preferably 55% or less, still more preferably 50% or less.

$Ta_2O_5$ is an optional component. The $Ta_2O_5$ content is from 0 to 30% assuming the total of the matrix composition is 100%. When the $Ta_2O_5$ content is 1% or more, the refractive index can be increased. The $Ta_2O_5$ content is more preferably 5% or more, still more preferably 10% or more, especially preferably 15% or more.

When the $Ta_2O_5$ content is 30% or less, the devitrification temperature can be lowered and moreover, the raw material cost can be reduced. The $Ta_2O_5$ content is preferably 25% or less, more preferably 20% or less, still more preferably 15% or less, especially preferably 10% or less.

The optical glass of this embodiment can contain, as an optional component, alkali metal components ($Li_2O+Na_2O+K_2O$). The content of $Li_2O+Na_2O+K_2O$ is from 0 to 20% assuming the total of the matrix composition is 100%. When $Li_2O+Na_2O+K_2O$ is 2% or more, $T_2$ is readily lowered, the melting temperature is low, and coloration is controlled. The content of $Li_2O+Na_2O+K_2O$ is preferably 4% or more, more preferably 6% or more, still more preferably 8% or more, especially preferably 10% or more. When the content of $Li_2O+Na_2O+K_2O$ is 20% or less, the devitrification temperature is lowered, and preferable production characteristics are obtained. The content of $Li_2O+Na_2O+K_2O$ is preferably 15% or less, more preferably 10% or less, still more preferably 8% or less, especially preferably 6% or less.

In the optical glass of this embodiment, among alkali metal components ($Li_2O$, $Na_2O$, $K_2O$), $Li_2O$ is a component capable of enhancing the strength of the glass, but if its amount is too large, $T_2$ is readily lowered, and devitrification is likely to occur. Accordingly, in the optical glass of this embodiment, the value of the ratio $Li_2O/(Li_2O+Na_2O+K_2O)$ is preferably 0.45 or less in mass % based on oxides. When $Li_2O/(Li_2O+Na_2O+K_2O)$ is 0.45 or less, $T_2$ is likely to be high, devitrification is less likely to occur, and ease of formability of the glass is enhanced. $Li_2O/(Li_2O+Na_2O+K_2O)$ is more preferably 0.4 or less, still more preferably 0.35 or less, especially preferably 0.3 or less.

$Li_2O$ is an optional component. The $Li_2O$ content is preferably from 0 to 15% assuming the total of the matrix composition is 100%. When $Li_2O$ is contained, the strength (Kc) and crack resistance (CIL) can be enhanced. The $Li_2O$ content is more preferably 0.5% or more, still more preferably 1% or more, yet still more preferably 3% or more, especially preferably 5% or more. On the other hand, when the $Li_2O$ content is 15% or less, the devitrification temperature is lowered, and preferable production characteristics are obtained. The $Li_2O$ content is preferably 10% or less, more preferably 7% or less, still more preferably 5% or less, especially preferably 4% or less.

SrO is an optional component. The SrO content is preferably from 0 to 30% assuming the total of the matrix composition is 100%. By containing the SrO component, the refractive index of the glass can be increased. The SrO content is more preferably 1% or more, still more preferably 3% or more, yet still more preferably 5% or more, especially preferably 10% or more. When the content is 30% or less, the devitrification temperature is lowered, and preferable production characteristics are obtained. The SrO content is more preferably 20% or less, still more preferably 15% or less, yet still more preferably 10% or less, especially preferably 5% or less.

BaO is an optional component. The BaO content is preferably from 0 to 50% assuming the total of the matrix composition is 100%. By containing the BaO component, the refractive index of the glass can be increased. The content is more preferably 1% or more, still more preferably 3% or more, yet still more preferably 5% or more, especially preferably 10% or more. When the content is 50% or less, the devitrification temperature is lowered, and preferable production characteristics are obtained. The BaO content is more preferably 35% or less, still more preferably 20% or less, yet still more preferably 15% or less, especially preferably 10% or less.

$TiO_2$ is an optional component. The $TiO_2$ content is from 0 to 55% assuming the total of the matrix composition is 100%. When $TiO_2$ is contained, the refractive index of the glass can be increased, and the stability of the glass can be enhanced. The $TiO_2$ content is preferably 1% or more, more preferably 5% or more, still more preferably 10% or more, especially preferably 15% or more.

When the $TiO_2$ content is 55% or less, the devitrification temperature is lowered, and coloration of the glass is controlled. The $TiO_2$ content is preferably 35% or less, more preferably 25% or less, still more preferably 15% or less, especially preferably 10% or less.

$ZrO_2$ is an optional component. The $ZrO_2$ content is from 0 to 55% assuming the total of the matrix composition is 100%. When $ZrO_2$ is contained, the refractive index of the glass can be increased, and the chemical durability can be enhanced. The $ZrO_2$ content is preferably 1% or more, more preferably 5% or more, still more preferably 10% or more, especially preferably 15% or more.

When the $ZrO_2$ content is 55% or less, the devitrification temperature is lowered, and preferable production characteristics are obtained. The $ZrO_2$ content is preferably 30% or less, more preferably 20% or less, still more preferably 15% or less, especially preferably 10% or less.

$WO_3$ is an optional component. The $WO_3$ content is from 0 to 55% assuming the total of the matrix composition is 100%. When $WO_3$ is contained, the refractive index of the glass can be increased. The $WO_3$ content is preferably 1% or more, more preferably 3% or more, still more preferably 5% or more, especially preferably 10% or more.

When the $WO_3$ content is 55% or less, the devitrification temperature is lowered, and coloration of the glass is controlled. The $WO_3$ content is preferably 30% or less, more preferably 20% or less, still more preferably 15% or less, especially preferably 10% or less.

$Bi_2O_3$ is an optional component. The $Bi_2O_3$ content is from 0 to 55% assuming the total of the matrix composition is 100%. When $Bi_2O_3$ is contained, the refractive index of the glass can be increased. The $Bi_2O_3$ content is preferably 1% or more, more preferably 5% or more, still more preferably 5% or more, especially preferably 10% or more.

When the $Bi_2O_3$ content is 55% or less, the devitrification temperature is lowered, and coloration of the glass can is controlled. The $Bi_2O_3$ content is preferably 35% or less, more preferably 25% or less, still more preferably 15% or less, especially preferably 10% or less.

$TeO_2$ is an optional component. The $TeO_2$ content is from 0 to 30% assuming the total of the matrix composition is 100%. When $TeO_2$ is contained, the refractive index of the glass can be increased. The $TeO_2$ content is preferably 1% or more, more preferably 5% or more, still more preferably 10% or more, especially preferably 15% or more.

When the $TeO_2$ content is 55% or less, the devitrification temperature can be lowered and moreover, the material cost can be reduced. The $TeO_2$ content is preferably 30% or less, more preferably 20% or less, still more preferably 15% or less, especially preferably 10% or less.

By containing $Ln_2O_3$ (Ln is one or more selected from the group consisting of Y, La, Gd, Yb and Lu), the refractive index of the glass can be increased. The $Ln_2O_3$ content is preferably 1% or more, more preferably 3% or more, still more preferably 5% or more, especially preferably 10% or more. On the other hand, when the $Ln_2O_3$ content is 55% or less assuming the total of the matrix composition is 100%, the devitrification temperature is lowered, and preferable production characteristics are obtained. The $Ln_2O_3$ content is in total preferably 35% or less, more preferably 20% or less, especially preferably 15% or less.

Examples of (3) the $P_2O_5$-based optical glass include a glass containing from 10 to 70 mass % of $P_2O_5$ and containing, as the high refractive index component, 1% or more of at least one selected from the group consisting of $Nb_2O_5$, $Ta_2O_5$, $Li_2O$, SrO, BaO, $TiO_2$, $ZrO_2$, $WO_3$, $Bi_2O_3$, $TeO_2$ and $Ln_2O_3$ (Ln is at least one selected from the group consisting of Y, La, Gd, Yb and Lu).

$P_2O_5$ is a glass forming component constituting the glass, and its action of imparting producible stability to the glass and reducing the glass transition temperature and liquid phase temperature is large. However, if the $P_2O_5$ content is less than 10% assuming the total of the matrix composition is 100%, sufficient effects are not obtained. The $P_2O_5$ content is preferably 15% or more, more preferably 20% or more, still more preferably 30% or more, especially preferably 40% or more. In addition, when the $P_2O_5$ content is 70% or less, good chemical durability is obtained. The $P_2O_5$ content is preferably 65% or less, more preferably 60% or less, still more preferably 55% or less, especially preferably 50% or less.

The high-refractive-index component is the same as that of (2) $SiO_2$ above and therefore, description thereof is omitted.

Furthermore, it is preferable that the optical glass of this embodiment contains at least one of $Sb_2O_3$ and $SnO_2$. These are not an essential component but can be added for the purpose of, for example, adjusting the refractive index property, enhancing the meltability, controlling coloration, increasing the transmittance, and improving the clarity and chemical durability. In the case where these components are contained, the content thereof is in total preferably 5% or less, more preferably 3% or less, still more preferably 1% or less, especially preferably 0.5% or less.

[Optical Glass and Production Method of Glass Molded Body]

The optical glass of this embodiment is produced, for example, as follows.

First, raw materials are weighed to give the predetermined glass composition above and uniformly mixed. The obtained raw material mixture is charged into a continuous melting furnace and heated by a burner to melt the raw material mixture and after homogenization by refining, stirring, etc., the melt is flowed out from the continuous melting furnace, cooled and solidified to obtain the optical glass of this embodiment.

When cooled, conditions are set so that the difference (Tf−Tg) between Tf and Tg of the optical glass is 0° C. or more in this embodiment. In order to satisfy such a relationship, the manufacturing conditions are set so that Tf is raised. For example, the cooling rate in the temperature region from (Tg+100° C.) to around (Tg−150° C.) relating to the fictive temperature is made rapid. The cooling rate is preferably 2° C./min or more.

Furthermore, when the above conditions are satisfied, the optical glass can be made into a glass plate by forming the molten glass into a plate shape by a known forming method such as float method and roll-out method. In addition, a glass molded body can be fabricated using means such as reheat press molding or precise press molding. More specifically, a lens preform for a mold-press molding is fabricated from the optical glass, and this lens preform may be subjected to reheat press molding and then polishing to fabricate the glass molded product, or for example, the lens preform fabricated by polishing may be subjected to precise press molding to fabricate the glass molded product. The means to fabricate the glass molded product is not limited to these means.

As for the melting method, the continuous melting method described above is suitable, but other than this method, the optical glass may also be obtained by a conventional known method. For example, a mixture obtained by mixing raw materials may be put in a platinum crucible, a quartz crucible or an alumina crucible and roughly melted. After that, the melt may be put in a gold crucible, a platinum crucible, a platinum alloy crucible, a reinforced platinum crucible or an iridium crucible, melted at a temperature ranging from 1,200 to 1,400° C. for 2 to 10 hours, homogenized by refining, stirring, etc. to effect foam breaking, etc., then cast on a metal mold, and slowly cooled to obtain the optical glass.

An optical member such as the thus-fabricated glass plate or glass molded body is useful for various optical elements and, among others, is suitably used for (1) wearable device, for example, glasses with projector, a glasses-type or goggle-type display, a light guide used for a virtual reality and augmented reality display device, a virtual image display device, etc., a filter, and a lens, and (2) a lens, a cover glass, etc. used for a vehicle-mounted camera or a robots' visual sensor. Even in applications exposed to severe environment, such as vehicle-mounted camera, the optical member is suitably used. In addition, the optical member is also suitably used for applications such as organic EL glass substrate, wafer level lens array substrate, lens unit substrate, lens forming substrate by an etching method, and optical waveguide.

The optical glass of this embodiment described hereinabove has a high refractive index, a low density, and good production characteristics and is suitable as an optical glass for wearable device, for vehicle mounting, and for robot mounting.

Examples

A Si—Nb-based glass was melted using raw materials such as oxide to obtain an optical glass formed in block shape. This optical glass was crushed to produce a cullet raw material. From the cullet raw material, necessary amounts for samples of Examples 1 to 7 were weighed, and each weighed raw material was put in a platinum crucible, melted at about 1,400° C. for about 5 hours, refined, stirred, then cast into a carbon frame, kept at the holding temperature (Tk) and retention time shown in Table 2, and cooled at the cooling rate shown in Table 2 from the holding temperature to normal temperature (about 25° C.) to obtain plate-like molded bodies of Examples 1 to 7. Samples having a thickness of 0.5 mm, a width of 30 mm, and a depth of 10 mm were created from the plate-like molded bodies. Examples 1 to 4 are Working Examples, and Examples 5 to 7 are Comparative Examples.

[Properties]

With respect to each sample obtained above, the fictive temperature (Tf), glass transition temperature (Tg), coefficient of thermal expansion (α), refractive index ($n_d$), crack initiation load, crack initiation load in precise annealing, difference between the minimum value and the maximum value of the refractive index, and difference between the minimum value and the maximum value of the refractive index indicator value N were measured as follows. The results obtained are shown together in Table 2. Note that the blank column is an unmeasured property.

Fictive Temperature (Tf): A plurality of specimens having the same composition and shape as the sample in each of Examples above were created, put in an infrared concentrated heating furnace, heated up to a temperature at which the glass structure was relaxed in short time (for example, glass transition temperature+100° C. or more), maintained, cooled to a predetermined holding temperature (Tk) that was a temperature lower than the heating temperature, kept at this Tk for about 1 hour, and then rapidly cooled to room temperature (for example, at a cooling rate of about 100° C./min).

The test above was performed by setting Tk at a plurality of different temperatures (for example, (Tg+60° C.), (Tg+30° C.), (Tg)), and the refractive index obtained here of each glass was measured. Furthermore, each specimen was kept at Tk for about 2 hours and then rapidly cooled at the same cooling rate as above, and it was confirmed that there was no change in the refractive index (confirmed that Tf is equal to Tk). When no change in the refractive index could be confirmed, a calibration curve was created from the relationship between Tf and the refractive index obtained above of each specimen. When a change in the refractive index was observed, the holding time at Tk was prolonged until the refractive index was not changed.

Next, the sample obtained above of each Example was measured for the refractive index, and Tf was determined using the calibration curve created.

Glass Transition Temperature (Tg): The glass transition temperature is a value measured using a differential dilatometer (TMA) and was determined according to JIS R3103-3 (2001).

Coefficient of Thermal Expansion (α): The coefficient of linear thermal expansion in the range of 30 to 350° C. was measured using a differential dilatometer (TMA), and the average coefficient of linear thermal expansion in the range of 30 to 350° C. was determined according to JIS R3102 (1995).

Refractive Index ($n_d$): The glass of the molded body obtained in each Example was processed into a triangle-shaped prism having a thickness of 10 mm with one side being 30 mm and measured by a refractometer (manufactured by Kalnew Corporation, device name: KPR-2000).

Crack Initiation Load: In a constant temperature and humidity bath kept at a humidity of 30% and a temperature of 25° C., a Vickers indenter set at a load of 10, 25, 50, 100 and 200 g was pressed against the glass surface (optical polished surface) for 15 seconds, and after 15 seconds, the number of cracks generated from four corners of the indentation was counted (4 cracks at the maximum per one indentation). The pressing was repeated 20 times (that is, the indenter was pressed 20 times) at each load, and after counting the total number of cracks, the crack initiation rate was determined by total number of crack initiations/80. The obtained crack initiation was potted vs. load, and the load at which the crack initiation rate was 50% when fitting a sigmoid function by means of the least squares method was defined as the crack initiation load.

Crack Initiation Load in Precisely Annealed sample: The crack initiation load in precisely annealed sample was determined by the same method as above except that a glass obtained through melting and precise annealing of a raw material having the same composition as in each Example was used as the sample.

Here, in the precise annealing performed, the optical glass was put in a box-type electric furnace, heated up to Tg+30° C. (a temperature 30° C. higher than the glass transition temperature), kept for 1 hour, cooled to Tg−150° C. (a temperature 150° C. lower than the glass transition temperature) at a cooling rate of 0.1° C./min under program control, and allowed to naturally cool.

Difference (Δn) Between Minimum Value and Maximum Value of Refractive Index: As described in the detailed description above, a sample was cut out from a plate-like molded body, and a side surface was polished to create a measurement sample. The refractive index distribution on surface A of the measurement sample was calculated, and the difference between the minimum value and the maximum value was determined.

Difference Between Maximum Value and Minimum Value of Refractive Index Indicator Value N: On surface A of the measurement sample, the numerical value was measured along a direction passing the center of gravity of surface A and being perpendicular to the main surface for each of sections equally divided, and the refractive index indicator value N was calculated using formula (1). In the refractive index indicator values N obtained of each section, the difference between the minimum value and the maximum value was determined.

TABLE 2

|  | Example | | | | Comparative Example | | |
| --- | --- | --- | --- | --- | --- | --- | --- |
|  | Example 1 | Example 2 | Example 3 | Example 4 | Example 5 | Example 6 | Example 7 |
| Type of glass | Si—Nb-based | Si—Nb-based | Si—Nb-based | Si—Nb-based | Si—Nb-based | Si—Nb-based | Si—Nb-based |
| Glass transition temperature (° C.) | 590 | 590 | 590 | 590 | 590 | 590 | 590 |
| $\alpha$ (×$10^{-7}$/° C.) | 81 | 81 | 81 | 81 | 81 | 81 | 81 |
| Young's modulus (GPa) | 99 | 99 | 99 | 99 | 99 | 99 | 99 |
| Holding temperature (° C.) | 690 | 620 | 590 | 630 | 540 | 590 | 590 |
| Retention time | 1 min | 60 min | 60 min | 60 min | 72 h | 60 min | 60 min |
| Cooling rate (° C./min) | 100 | 100 | 100 | 100 | 100 | 1 | 0.1 |
| Refractive index | 1.7761 | 1.7776 | 1.7789 | 1.7769 | 1.7823 | 1.7799 | 1.7817 |
| Fictive temperature (° C.) | 642 | 617 | 595 | 628 | 538 | 579 | 548 |
| Fictive temperature-glass transition temperature (° C.) | 52 | 27 | 5 | 38 | −52 | −11 | −42 |
| Crack initiation load (mN) | 859 | 482 | 404 | 578 | 274 | 274 | 303 |
| Difference from that of precisely annealed sample (mN) | 557 | 179 | 101 | 276 | −28 | −28 | 0 |
| Difference between maximum value and minimum value of refractive index | $0.3 \times 10^{-5}$ | $2.0 \times 10^{-5}$ | $1.0 \times 10^{-5}$ | $0.3 \times 10^{-5}$ | $0.3 \times 10^{-5}$ | $2.0 \times 10^{-5}$ | $1.5 \times 10^{-5}$ |
| Difference maximum value and minimum value of refractive index indicator value | $0.4 \times 10^{-3}$ | $1.9 \times 10^{-3}$ | $1.1 \times 10^{-3}$ | $0.3 \times 10^{-3}$ | $0.5 \times 10^{-3}$ | $2.0 \times 10^{-3}$ | $1.6 \times 10^{-3}$ |
| Arithmetic mean roughness (Ra) (nm) | 0.3 | 0.5 | 0.3 | 0.4 | 0.5 | 0.5 | 0.4 |

In all optical glasses of Working Examples (Examples 1 to 4), the refractive index ($n_d$) is 1.55 or more and is a high refractive index. In these optical glasses, (Tf−Tg) is 0° C. or more, revealing that the strength was enhanced. Therefore, they are suitable as an optical glass used in a wearable device, in-vehicle camera or robotic vison.

On the other hand, in optical glasses of Examples 5 to 7 which are Comparative Examples, (Tf−Tg) is 0° C. or less and in turn, the strength is low.

A plate-like molded body was formed under the same conditions as in Example 1 by using the cullet raw material described above, and a sample having a thickness of 0.5 mm, a width of 40 mm and a depth of 25 mm was created and measured for the crack initiation load, as a result, the load was 850 mN which is a value exceeding 350 mN.

As seen from these results, the optical glass of this embodiment has a high refractive index and enhanced strength and is suitable as an optical glass used in a wearable device, mounted on a car, mounted on a robot, etc.

The invention claimed is:

1. An optical glass having a refractive index ($n_d$) of 1.55 or more,
    wherein a difference (Tf−Tg) between a fictive temperature (Tf) and a glass transition temperature (Tg) of the optical glass is 10° C. or more and 70° C. or less,
    wherein the optical glass has a maximum thickness of 0.01 mm or more and 0.8 mm or less,
    wherein the optical glass is an LaB-based optical glass or a $P_2O_5$-based optical glass,
    wherein the optical glass is obtained by a method wherein the cooling rate in the temperature region from (Tg+ 100° C.) to around (Tg−150° C.) is 2° C./min or more, and
    wherein the Tg of the optical glass is 500° C. or more and 800° C. or less.

2. The optical glass according to claim 1, having a crack initiation load L of 350 mN or more.

3. The optical glass according to claim 1, wherein the crack initiation load L of the optical glass is larger by 98 mN or more than a crack initiation load L0 of a glass having the same composition as the optical glass and being obtained through annealing at 0.1° C./min after melting.

4. The optical glass according to claim 1, having the refractive index ($n_d$) of more than 1.74.

5. The optical glass according to claim 1, having a plate-like shape or lens-like shape.

6. The optical glass according to claim 5, comprising main surfaces comprising a first main surface and a second main surface, and a side surface formed to be adjacent to the first main surface and the second main surface, wherein at least one of the main surfaces has an arithmetic mean roughness (Ra) of 2 nm or less.

7. The optical glass according to claim 6, having a plate-like shape and having an area of at least one of the main surfaces of 8 $cm^2$ or more.

8. An optical member comprising the optical glass according to claim 1.

9. A wearable device comprising the optical glass according to claim 1.

10. The optical glass according to claim 1, wherein the difference (Tf−Tg) between the fictive temperature (Tf) and the glass transition temperature (Tg) of the optical glass is 20° C. or more and 70° C. or less.

* * * * *